United States Patent [19]

Samaras et al.

[11] Patent Number: 4,649,928
[45] Date of Patent: Mar. 17, 1987

[54] NOISE-IMMUNE BLOOD PRESSURE MEASUREMENT TECHNIQUE AND SYSTEM

[75] Inventors: George M. Samaras, Columbia; Otis R. Blaumanis, Sparks; H. William Van Horn, Elkridge, all of Md.

[73] Assignee: GMS Engineering Corporation, Columbia, Md.

[21] Appl. No.: 789,784

[22] Filed: Oct. 21, 1985

[51] Int. Cl.⁴ .............................................. A61B 5/02
[52] U.S. Cl. ..................... 128/672; 128/681
[58] Field of Search ............... 128/672, 677, 679, 680, 128/681, 682, 683

[56] References Cited

U.S. PATENT DOCUMENTS

| | | | |
|---|---|---|---|
| 2,193,945 | 3/1940 | Strauss et al. | |
| 3,095,872 | 7/1963 | Tolles | 128/672 |
| 3,095,872 | 7/1963 | Tolles | |
| 3,118,440 | 1/1964 | de Dobbeleer | |
| 3,348,534 | 10/1967 | Marx et al. | 128/679 |
| 3,581,734 | 6/1971 | Croslin et al. | 128/679 |
| 3,581,734 | 6/1971 | Croslin | |
| 3,741,199 | 6/1973 | Sharpe | |
| 3,831,590 | 8/1974 | Boyle et al. | 128/672 |
| 3,903,872 | 9/1975 | Link | 128/681 |
| 3,908,639 | 9/1975 | McIntyre | 128/672 |
| 4,080,966 | 3/1978 | McNally et al. | |
| 4,245,648 | 1/1981 | Trimmer et al. | |
| 4,271,843 | 6/1981 | Flynn | 128/681 |
| 4,349,034 | 9/1982 | Ramsey, III | 128/681 |
| 4,408,614 | 10/1983 | Weaver et al. | 128/682 |
| 4,418,700 | 12/1983 | Warner | 128/672 |
| 4,437,470 | 3/1984 | Prost | |
| 4,461,266 | 7/1984 | Hood, Jr. et al. | |
| 4,564,020 | 1/1986 | Link | 128/677 |

FOREIGN PATENT DOCUMENTS 2092309  8/1982  United Kingdom ............... 128/672

OTHER PUBLICATIONS

Gordon Fuller, Analytic Geometry and Calculus, 1964, pp. 92-113.

Primary Examiner—Edward M. Coven

[57] ABSTRACT

An apparatus and method for non-invasive, noise insensitive blood pressure determination which is useful in a battlefield or emergency vehicle environment. The system features an occlusion bladder and a sensing bladder both adapted to fit over the limb of a patient. The pressure in the occlusion bladder is raised to a value which prevents flow and is then gradually decreased. The pressure in both bladders is monitored. When the pressure in the sensing bladder reaches a minimum value, the pressure in the occlusion bladder is equal to the systolic pressure. The first, second, and third time derivatives of the pressure in the sensing bladder are monitored. The first derivative is useful in identifying the minimum in the pressure in the sensing bladder. When the third time derivative of the pressure in the sensing bladder passes through zero, the pressure in the occlusion bladder is equivalent to the mean arterial pressure. The diastolic pressure can be calculated from the values of the systolic and mean arterial pressures.

28 Claims, 3 Drawing Figures

NOISE-IMMUNE BLOOD PRESSURE MEASUREMENT TECHNIQUE AND SYSTEM

GOVERNMENT INTEREST

The U.S. Government may have rights in this invention under Contract No. DAMD17-83-C-3064 with the U.S. Army Medical Research and Development Command.

FIELD OF THE INVENTION

This invention relates to blood pressure measurement systems and methods. More particularly, the invention relates to a blood pressure measurement system which is very much more noise immune than prior art systems, and which is therefore much more useful in battlefield, emergency vehicle, air transport and other noisy situations in which conventional measurements of blood pressure are unsuitable.

BACKGROUND AND OBJECTS OF THE INVENTION

For many years it has been recognized that blood pressure measurement provides a very useful indication of the relative health of a patient, especially in traumatic situations. Typically, emergency medical personnel find it desirable to monitor such things as a patient's blood pressure, respiration, capillary refill rate, dilation of the pupils, and temperature in traumatic situations such as on a battlefield, in an emergency vehicle en route to a hospital after an auto accident, or the like. Blood pressure measurement is very difficult under these circumstances using conventional non-invasive techniques.

The most common blood pressure measurement technique involves listening to the patient's pulse with a stethoscope while varying the pressure in an occlusion bladder placed over a limb, typically the arm. Initially, the pressure in the occlusion bladder is increased until blood flow stops. That is, the pressure in the occlusion bladder is raised above the systolic pressure. The bladder pressure is then gradually reduced over a few seconds, while the patient's pulse is monitored. The characteristic sounds of pulses in the bloodstream are referred to as "Korotkoff noises." When a first such noise is detected, the pressure in the bladder at that time corresponds to the systolic pressure, the pressure exerted by the heart during its contraction, when blood is pumped from the chambers of the heart. A subsequent change in the characteristic sound of the pulse, when the Korotkoff noises cease, indicates that the pressure in the bladder is equal to the diastolic pressure, the pressure exerted by the heart on the blood vessels during the heart's dilation, when the chambers of the heart relax and refill with blood. To audibly detect pulses, i.e. to hear the Korotkoff noises, requires a relatively quiet environment. Accordingly, blood pressure measurement techniques using stethoscopes to detect these sounds are best performed in a hospital or similar environment. They are particularly unsuitable for use in an emergency vehicle, on a battlefield, or the like, where the noise level is very high.

It will be appreciated by those skilled in the art that "noise" in this context includes audible noise, which interferes with the ability of the physician or emergency medical personnel to hear the Korotkoff noises in the stethoscope, as well as physical motion of the patient either with respect to the physician or during transport in a vehicle. Such motion, of course, generates additional variations in pressure which can mask or obscure pulses in the blood pressure, or which can sound to the physician like Korotkoff noises, thus causing an inaccurate measurement to be made.

Accordingly it is an object of the invention to provide a blood pressure measurement system which does not require a physician to listen to a patient's pulse through a stethoscope or the like.

There have been developed a large number of methods and apparatus for mechanized measurement of a patient's blood pressure. Some of these are invasive, i.e. involve insertion of a catheter or the like into an artery. Such invasive methods are undesirable for obvious reasons. All of the non-invasive measurement techniques of which the present inventors are aware, mechanized or not, involve detection of the pulses caused by the pumping action of the heart. Whether detected by a physician using a stethoscope or by a machine, detection of pulses is rendered difficult or impossible by noise, again including physical motion of the patient.

Accordingly, it is an object of the invention to provide a method of measuring the blood pressure of a patient which does not involve detection of the pulses caused by the pumping action of the heart, so as to realize substantial noise immunity.

A number of patents have been issued on automated devices for measuring the blood pressure of a patient. One such device is taught in U.S. Pat. No. 4,437,470 to Prost. Prost teaches controlling the blood pressure in a patient's finger by means of an occluding cuff and monitoring the transparency of the skin area downstream of the occluding cuff. The occluding cuff pressure is gradually varied over a period of on the order of 20 seconds, so that blood flow is at first interrupted and is then gradually resumed. The instrument comprises means for monitoring the pressure as a function of time and identifying certain inflection points in the transparency curve as indicating the systolic and diastolic pressure. In particular, Prost teaches an empirical formula for combining pressure measurements which he states has been experimentally determined to provide a more accurate measure of the systolic pressure than does any particular one of the inflection points.

Prost, however, still requires that the pulse be detected (column 5, lines 14-22, and claim 4). Accordingly, the Prost device is not suitable for use in a noisy environment such as an emergency vehicle or on a battlefield.

The Croslin et al. U.S. Pat. No. 3,581,734 shows an apparatus for measuring blood pressure comprising a larger cuff for occluding the brachial artery and a smaller cuff located on the forearm for continuously detecting the magnitude of blood pulses. A pressure transducer on the upper cuff provides measurement of systolic and diastolic pressures. The technique employed requires detection of the pulse, which is performed by the smaller cuff which controls the indicating circuitry.

The McNally et al. U.S. Pat. No. 4,080,966 shows an appartus and method for regulating blood pressure in which the mean arterial pressure is determined in a conventional manner, by filtering the blood pressure, which is measured using a conventional directly invasive technique. The filtering is preferably accomplished by integration.

The Doll U.S. Pat. No. 4,134,396 covers a method for measuring steady flow of blood using a non-invasive flow meter which relies on electronic methods for detecting pulses in the flow.

The Hood, Jr. U.S. Pat. No. 4,461,266 shows a device for measuring blood pressure which relies on determination of mean arterial pressure. The Hood device also requires detection of the pulse.

It is a further object of the invention to provide a non-invasive blood pressure measurement technique which provides accurate values for diastolic and systolic pressure without need of detection of the pulses in the blood flow, which is suitable for a noisy environment, which is simple and relatively inexpensive, and which is adaptable to blood pressure sensing without removal of the patient's garments, including relatively heavy uniforms or oversuits, so as to be useful in a wide variety of conditions and circumstances.

Classically, the systolic and diastolic pressures have been considered the most relevant information concerning a person's blood pressure. More recently, however, the mean arterial pressure, that is, the mean value for the blood pressure, has become of increased interest to some medical personnel, typically anesthesiologists and the like. Accordingly, it is an object of the invention to provide an instrument which provides accurate values for the systolic, diastolic and mean arterial blood pressures of a patient, and which employs a non-invasive technique which does not require detection of pulses in the blood flow.

SUMMARY OF THE INVENTION

The present invention satisfies the needs of the art and objects of the invention discussed above by its provision of an improved non-invasive, noise-immune blood pressure monitoring apparatus which determines values for the systolic, diastolic and mean arterial pressures without detection of the pulse. The device comprises a pair of bladders adapted to slip over a patient's limb. An occlusion bladder at the proximal end of the limb (e.g., on the upper arm) is inflated to a pressure substantially higher than the systolic blood pressure of a patient, such that blood flow is stopped. The lower sensing bladder (e.g., on the forearm) is inflated to a nominal value. The pressure in the occlusion bladder is allowed to gradually decrease over a period of a minute or more. The pressures in both the upper occlusion bladder and the lower sensing bladder are then monitored. The pressure in the sensing bladder is filtered to remove the pulses from the waveform. When the pressure in the sensing bladder drops to a minimum, the pressure in the occlusion bladder is equal to the systolic pressure. The first, second and third time derivatives of the pressure in the sensing bladder are also monitored. When the third derivative passes through zero, indicating a peak in the second derivative and an inflection point in the pressure in the sensed bladder, the pressure in the occlusion bladder is equal to the mean arterial pressure. The diastolic pressure may be calculated from this value and that previously detected for the systolic pressure, according to a well known relation.

In the preferred embodiment, the invention is implemented using a microprocessor, controlling a number of valves and a pump, and comprises means for monitoring the pressure in the occlusion and sense bladders, for calculating the derivatives required, and for providing a display responsive thereto.

BRIEF DESCRIPTION OF THE DRAWINGS

The invention will be better understood if reference is made to the accompanying drawings in which:

FIGS. 2(a) through 2(f) shows a number of typical signals useful in understanding the present invention, wherein:

FIG. 2(a) shows the pressure in the sense bladder S as a function of time;

FIG. 2(b) shows the pressure S after having been filtered, as a function of time;

FIG. 2(c) shows the first time derivative of S;

FIG. 2(d) shows the second time derivative of S;

FIG. 2(e) shows the third time derivative of S; and

FIG. 2(f) shows the pressure in the occlusion bladder O as a function of time.

DESCRIPTION OF THE PREFERRED EMBODIMENTS

The invention comprises a method and apparatus for measuring the systolic and diastolic blood pressure of a patient without requiring the necessity of detecting the pulses caused by the heart's pumping, such that the apparatus is useful in a demanding environment such as on a battlefield, in an emergency rescue vehicle, or the like. Clearly, to be suitable, the device must be simple, rugged, compact, easy to use and preferably relatively inexpensive.

Figure 1:
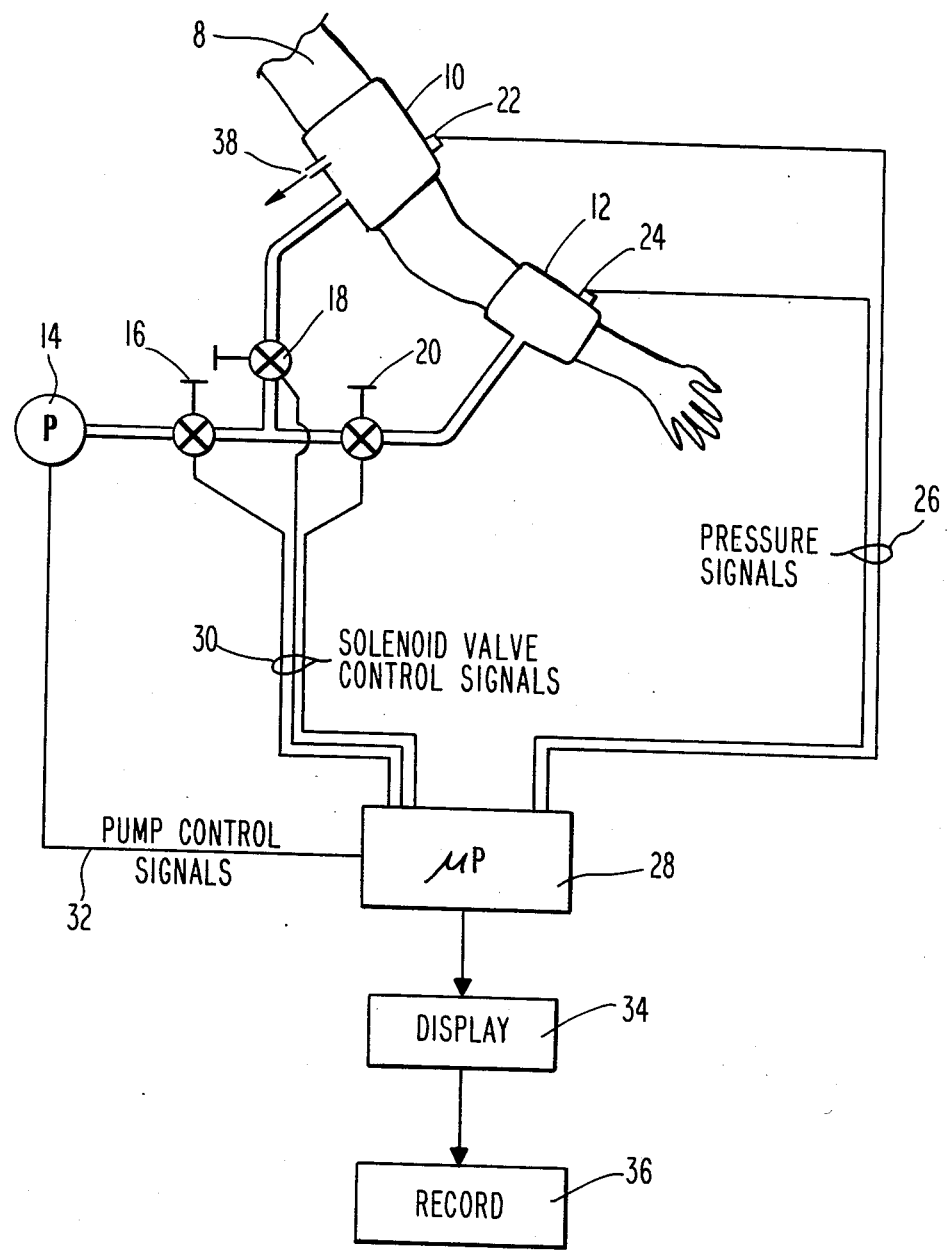
FIG. 1 shows an overall schematic view of a preferred embodiment of the apparatus of the present invention.

FIG. 1 shows a schematic drawing of apparatus which is suitable in this service. The apparatus according to the invention comprises a first or occlusion bladder 10 and a second or sensing bladder 12 which are placed over the limb 8 of a patient. The occlusion and sensing bladder 10 and 12, respectively (which may be conventional blood pressure cuffs, may be supplied with compressed air from pump 14 through a series of three solenoid valves 16, 18, and 20. To the occlusion bladder 10 is connected a pressure transducer 22 and to the sensing bladder 12 is connected a similar pressure transducer 24. Transducers 22 and 24 are connected as indicated generally at 26 to a microprocessor 28. (Electronic control and monitoring circuitry other than microprocessors per se would be suitable as well, and the term "microprocessor" when used herein should therefore be construed broadly). The valves 16, 18 and 20 are controlled by the microprocessor 28 as indicated at 30. Pump 14 is controlled by the microprocessor as well, as indicated at 32. The microprocessor provides an output display 34 and may also provide a printed record as indicated at 36.

According to the invention, it has been discovered that by monitoring the first, second and third time derivatives of the sensed pressure signal provided by the transducer 24 operatively connected to the sensing bladder 12, once can readily determine when the pressure in the occlusion bladder 10 is equal to the systolic and means arterial pressures. This enables calculation of the diastolic pressure using a well known relation. Accordingly, the microprocessor 28 monitors the pressure in the occlusion bladder 10 and the pressure in the sensing bladder 12, and also calculates the first, second and third time derivatives of the pressure in the sensing bladder 12.

In operation, as discussed in further detail in connection with FIG. 3 below, the pump 14 is first energized and the valves 16 and 20 are opened such that compressed air is supplied to the sensing bladder 12 to pump it to a suitably high pressure e.g. 60–70 mmHg. Valve 20 is then closed and valve 18 is opened, whereupon the occlusion bladder 10 is also inflated, typically to a pressure 60 to 70 mmHg above the anticipated systolic blood pressure of the patient. Valve 16 is then closed. Air is permitted to escape from the occlusion bladder 10 through a breathing orifice 38, which is sized such that the occlusion bladder 10 deflates at a relatively slow rate, typically 3–7 mmHg/sec; total deflation takes place over a period on the order of 1 to 2 minutes or as fast as 15 seconds. This enables the relatively slow changes in the pressure in the sense bladder 12 to be accurately recorded by storing the output from the transducer 24 at intervals of, e.g., ½ second.

Figure 2:
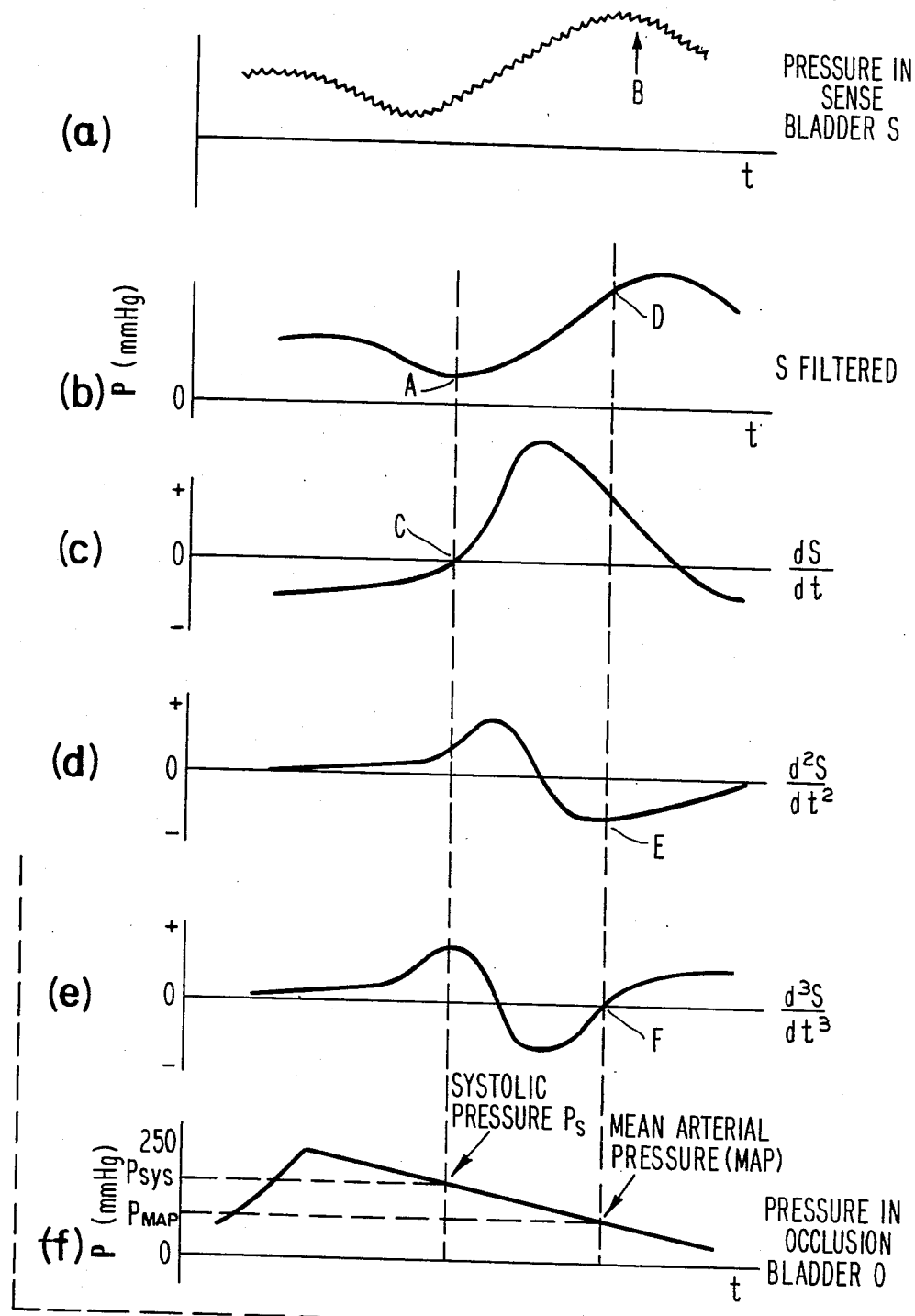
FIG. 2, comprising

FIG. 2 shows a number of waveforms useful in understanding the preferred method of the present invention. FIG. 2(a) shows the signal S indicative of changing pressure in the sense bladder 12 as a function of time. The amplitude of the signal S is generally indicative of the blood volume in the limb. Thus, FIG. 2(a) also indicates a change in blood volume with time. For comparison purposes, FIG. 2(f) shows the pressure O in the occlusion bladder 10 for the same period of time. As can be seen, as the pressure O in the occlusion bladder 10 is increased, due to the pumping by pump 14 of air thereto, the pressure in the sense bladder 12 gradually decreases as blood is driven out of the limb. Because blood evacuates the limb, limb volume decreases beneath the sensing bladder 12, decreasing pressure within the sensing bladder. This continues even while the pressure O begins to drop, until the pressure S drops to a local minimum, and therafter begins to increase. The minimum value in the pressure in sense bladder 12 occurs when the pressure in the occlusion bladder 10 is equal to the systolic pressure.

FIG. 2(b) represents the signals of FIG. 2(a) having been filtered to eliminate irregularities, as shown for example at B in FIG. 2(a), caused by the heart's pumping action. The filtering may be mechanical, by interposing a material which does not transmit high frequencies (such as foam rubber) between the sense bladder and the patient, electrical, by using Bessel filters, or mathematical, by means of the microprocessor. In any case, the filtering employed causes a time lag, resulting in the displacement of the minimum at A in FIG. 2(b) from that of FIG. 2(a). Point A in FIG. 2(b) thus indicates that the corresponding point on the record of the occlusion pressure O in FIG. 2(f) is the systolic pressure $P_S$. The filtered pressure signal may be referred to as the "static" pressure.

FIGS. 2(c)–2(e) show respectively the first, secnd and third time derivatives $$\frac{dS}{dt}, \frac{d^2S}{dt^2}, \text{ and } \frac{d^3S}{dt^3}$$

of the filtered sensed pressure S. The minimum in the pressure S in the sense bladder 12 noted at point A of FIG. 2(b) can most conveniently be located by realizing that it corresponds to the zero-crossing point C of the first time derivative $$\frac{dS}{dt}$$

of the filtered pressure signal, as shown in FIG. 2(c).

According to an important aspect of the present invention, the applicants have realized that there is an inflection point at D in the curve of the filtered sense pressure S (FIG. 2(b)). ("Inflection point" is used herein as conventional mathematical terminology to indicate a sudden change in the curve). The inflection at point D is believed to be caused by the fact that the maximum rate of change of volume in the limb (as shown by $$\frac{d^2S}{dt^2}$$), the volume being represented by S, occurs at the maximum "driving force" (i.e., the mean circulatory pressure). This is generally understood as the physical meaning of the mean arterial pressure (MAP). This confirms the identification of the inflection point D with MAP. Our experiments comparing conventional blood pressure measurement equipment to that of our invention further support this conclusion.

The inflection point D may be detected, according to another aspect of the invention, by realizing that it corresponds to the negative peak in the second time derivative $$\frac{d^2S}{dt^2}$$

of the filtered pressure S, as shown at E in FIG. 2(d). Point E, in turn, may be conveniently detected by noting that point E corresponds to the zero crossing point F of the third time derivative $$\frac{d^3S}{dt^3}$$

of the pressure signal S, as shown in FIG. 2(e). Accordingly, at point F, when the positive going third time derivative of the pressure signal crosses zero, the pressure O in the occlusion bladder 10 is the mean arterial pressure (MAP), as indicated in FIG. 2(f).

From the values for MAP and systolic pressure $P_S$, the diastolic pressure $P_D$ can be calculated using the well-known relation $P_D = \frac{1}{2}(3 \text{ MAP} - P_S)$. This equation will be recognized by those skilled in the art as the conventional definition of the mean arterial pressure (MAP).

Figure 3:
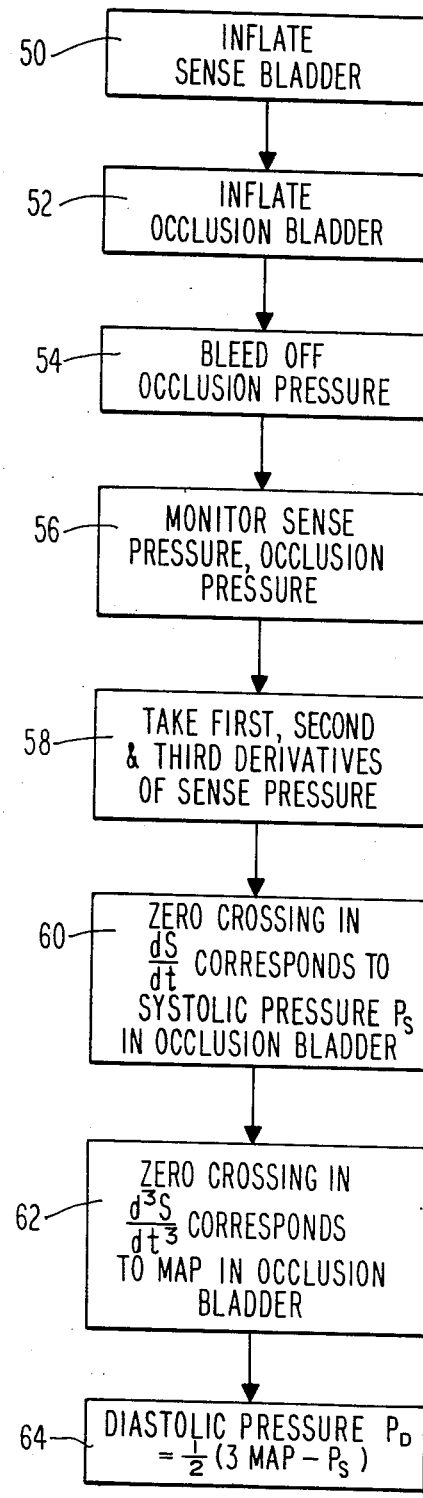
FIG. 3 shows a flowchart of the steps performed according to a preferred embodiment of the method of the present invention.

FIG. 3 shows the steps in the preferred method of the present invention. At 50, the sense bladder 12 is inflated by the pump 14, and at 52 the occlusion bladder 10 is similarly inflated. Thereafter, at 54, the occlusion pressure is steadily but controllably reduced by way of the orifice 38. Throughout this process the pressure signals from transducer 24 on the sense bladder 12 and from transducer 22 on the occlusion bladder 10 are monitored as noted at 56. The first, second and third time derivatives of the pressures in the sense bladder are calculated as indicated at 58. When the first derivative $$\frac{dS}{dt}$$

crosses through zero, the pressure in the occlusion bladder is equal to the systolic pressure $P_S$, as noted at 60. When the third derivative $$\frac{d^3S}{dt^3}$$

crosses zero, the pressure in the occlusion bladder is equal to the mean arterial pressure (MAP), as noted at 62. Finally, the diastolic pressure $P_D$ can be calculated using the relation $P_D=\frac{1}{2}$ (3 MAP$-P_S$), as noted at 64. The pulse pressure can also then be calculated by subtraction of the diastolic pressure from the systolic pressure. The results may then be output to an operator in any desired way, e.g. by use of a display, a printout, or the like.

It will be appreciated by those skilled in the art that there has been described a method for detecting systolic and diastolic blood pressures which does not require detection of pulses in the pressure. In fact, pulse information is deliberately filtered out of the signals so as to avoid inaccuracy caused thereby, as well as to remove any high frequency noise which might otherwise affect the system. The filtering can be mechanical, by use of a material (e.g., foam rubber) between the patient's limb and the sensing cuff which does not transmit higher frequencies; electronic, as by RC networks; or digital, implemented by the microprocessor. Accordingly, only low frequency signal components on the order of 1 Hz are of interest. Since most ambient noise is of much higher frequency, the system of the invention is not susceptible to most sources of noise. Further, it will be recognized by those skilled in the art that a large number of microprocessor systems and associated analog-to-digital converters and the like are suitable for implementing the invention. Such implementation is well within the skill of the art at this time, given the above disclosure of the invention. The fact that only very low frequency information is required means that the transducers 22 and 24 may be devices of very minimal sophistication. Similarly, the other hardware required for implementation of the invention, cuffs 10 and 12, valves 16, 18, and 20 and the pump 14 are all very straightforward and readily available.

In an alternate embodiment of the invention, it appears likely that analog circuit elements may be desirable to perform most of the functions of the microprocessor. These would include analog differentiator circuits and comparators for providing output signals for controlling display units. In particular, display units are now available which provide a decimal read-out which is proportional to an analog voltage supplied thereto. Therefore, the system of the invention could be implemented by providing comparators to detect when the output signals of differentiators calculating the first and third derivatives of the sense bladder pressure signal are equal to zero, and for communicating the signal from the occlusion bladder pressure transducer 22 to the display device at those times. This would be sufficient to provide indication of the systolic pressure and MAP values. The diastolic pressure could then be readily calculated by an operator, or by a very simple dedicated processor device.

Therefore, while a presently preferred embodiment of the invention has been described in detail, this should not be taken as a limitation on the scope of applicant's invention, which should only be measured by the following claims.

What is claimed is:

1. A method for the non-invasive sensing of the diastolic and systolic blood pressures of a patient, said method comprising the steps of:
   installing a proximal occlusion bladder and a distal sensing bladder on a limb of the patient;
   inflating said occlusion and sensing bladders;
   allowing said occlusion bladder to deflate controllably over time;
   monitoring a pressure in the sensing bladder;
   filtering out blood pulses from the monitored pressure to obtain a filtered pressure;
   determining when the filtered pressure in the sensing bladder reaches a minimum, and identifying the pressure in the occlusion bladder at that time as the systolic pressure;
   determining when the filtered pressure in the sensing bladder passes through an inflection point, and identifying the pressure in the occlusion bladder at that time as the mean arterial pressure; and
   calculating the diastolic pressure from said systolic and means arterial pressures.

2. The method of claim 1 wherein said step of determining when the filtered pressure in the sensing bladder reaches a minimum includes the step of taking the first time derivative of the filtered pressure in the sensing bladder and determining when said first time derivative passes through zero.

3. The method of claim 1 wherein said step of determining when the filtered pressure in the sensing bladder passes through an inflection point includes the step of calculating the third time derivative of the filtered pressure in said sensing bladder, and determining when said third time derivative positively passes through zero.

4. The method of claim 1 wherein said step of monitoring the pressure in said sensing bladder is performed by microprocessor means.

5. The method of claim 4 wherein said microprocessor means controls the pressure in said occlusion bladder, determines said systolic and mean arterial pressures, calculates said diastolic pressure, and further displays values for the systolic and diastolic pressure.

6. A system for non-invasive, substantially noise-immune measurement of the blood pressure of a patient, comprising:
   first cuff means for occluding blood flow in a limb of the patient;
   second cuff means for sensing pressure in the limb and disposed between said first cuff means and the distal end of the limb;
   means for monitoring the pressure in said first cuff means;
   means for monitoring the pressure in said second cuff means;
   means for reducing the pressure in said first cuff means at a predetermined rate;
   means for filtering out blood pulses from the monitored pressure in the second cuff means to obtain a filtered pressure;
   means for monitoring the time rate of change of the filtered pressure in said second cuff means, and for determining when said filtered pressure in said second cuff means passes through a minimum value and when said filtered pressure in said second cuff means exhibits an inflection point; and means for associating element values of the pressure in said first cuff means at the time at which the filtered pressure in said second cuff means passes through said minimum value and said inflection point which the systolic and mean arterial blood pressures of the patient, respectively.

7. The system of claim 6 wherein said means for monitoring the time rate of chanbe of filtered pressure in said second cuff means comprises means for taking the first, second, and third derivatives of said filtered pressure in said second cuff means, and comprises means for associating a zero crossing of the first time derivative of the filtered pressure in said second cuff means with the systolic pressure, and means for associating a positive zero crossing in the third time derivative of the filtered pressure in said second cuff means with the mean arterial pressure, and further comprises means for calculating a value for the diastolic pressure based on said values for the systolic and mean arterial pressures.

8. The system of claim 7 wherein said means for calculating the first, second and third time derivatives of the pressure in the second cuff means and for determining the systolic, diastolic, and means arterial pressures therefrom comprises a microprocessor.

9. The system of claim 8 wherein said microprocessor further comprises means for controlling the pressure in said first cuff means and said means for monitoring the pressure in said first cuff means and in the filtered pressure in said second cuff means.

10. The system of claim 9 further comprising means for generating a value for a pulse pressure.

11. The system of claim 8 further comprising means for providing operator-readable output values for the systolic, diastolic, and mean arterial pressures.

12. A non-invasive method of measuring blood pressure without detecting a pulse, comprising the steps of:
occluding a limb of a patient by applying pressure thereto;
releasing the pressure to the limb;
filtering out blood pulses from and measuring a filtered blood volume in the limb as the pressure in the limb is released; and
determining blood pressure from the filtered blood volume.

13. The method of claim 17, wherein said measuring step includes the step of determining the minimum filtered pressure in the limb.

14. The method of claim 13, wherein said minimum static pressure corresponds to the systolic blood pressure.

15. The method of claim 12, wherein said measuring step includes the step of determining when rate of change of blood volume in the limb is at a maximum value.

16. The method of claim 15, wherein the pressure in the occlusion bladder when the rate of change of blood volume in the limb is at a maximum value corresponds to the mean arterial pressure.

17. The method of claim 12, wherein said step of measuring includes the step of detecting the filtered pressure in the limb.

18. The method of claim 17, wherein said filtered pressure detecting step includes the step of detecting the systolic blood pressure.

19. The method of claim 18, wherein said static pressure detecting step further includes the step of detecting the means arterial blood pressure.

20. The method of claim 19, further comprising the step of calculating the diastolic blood pressure based on the detected values of the systolic blood pressure and the mean arterial blood pressure.

21. A non-invasive, noise immune method of measuring the blood pressure of a patient not requiring detection of pulses in the blood flow comprising the steps of:
occluding the limb of a patient by applying occlusion pressure thereto;
gradually releasing the pressure applied to the limb;
monitoring the occlusion pressure as a function of time;
monitoring the pressure sensed in a bladder about the limb;
filtering out blood pulses from said monitored sensed pressure; and
determining the patient's systolic, diastolic and mean arterial pressures from said filtered pressure.

22. The method of claim 21 comprising the step of detecting a minimum value reached by said filtered pressure and indicating that the occlusion pressure at the time of detection of the minimum value is equal to the patient's systolic blood pressure.

23. The method of claim 21 including the additional steps of:
locating an inflection point in the filtered pressure, and
determining the mean arterial pressure based on said inflection point.

24. The method of claim 23 wherein said inflection point is detected by monitoring time derivatives of said filtered pressure.

25. The method of claim 24 wherein first, second and third time derivatives of said filtered pressure are taken, and said inflection point is located by detecting a zero crossing of the third derivative.

26. A method of detecting the mean arterial pressure of a patient, comprising the steps of:
occluding a limb of the patient by applying pressure thereto;
gradually releasing pressure to said limb;
monitoring pressure in said limb downstream of the point at which said pressure is applied;
filtering out blood pulses from the monitored pressure to obtain a filtered pressure;
monitoring the sensed filtered pressure as a function of time to locate an inflection point therein; and
determining the mean arterial pressure based upon location of said inflection point.

27. The method of claim 26 whefein said inflection point is located by monitoring time derivatives of said sensed filtered pressure.

28. The method of claim 26 wherein said time derivatives include the first, second and third time derivative of the sensed filtered pressure and said mean arterial pressure is detected at a point at which the third derivative is positive going and equals zero.

* * * * *